United States Patent [19]
Geerke

[11] Patent Number: 5,658,474
[45] Date of Patent: Aug. 19, 1997

[54] METHOD AND APPARATUS FOR FORMING DISPENSER DELIVERY PORTS

[75] Inventor: Johan H. Geerke, Los Altos, Calif.

[73] Assignee: Alza Corporation, Palo Alto, Calif.

[21] Appl. No.: 358,230

[22] Filed: Dec. 16, 1994

[51] Int. Cl.⁶ .................................................. B23K 26/08
[52] U.S. Cl. .................................. 219/121.71; 219/121.8; 219/121.85; 424/467
[58] Field of Search ........................... 219/121.69, 121.7, 219/121.71, 121.72, 121.78, 121.8, 121.85; 264/400; 424/467, 473

[56] References Cited

U.S. PATENT DOCUMENTS

| | | | |
|---|---|---|---|
| 3,524,046 | 8/1970 | Brouwer | 219/384 |
| 3,549,733 | 12/1970 | Caddell | 219/121.69 |
| 3,764,775 | 10/1973 | Hasslinger et al. | |
| 3,786,224 | 1/1974 | Heywang et al. | 219/121.69 |
| 4,024,545 | 5/1977 | Dowling et al. | 347/259 |
| 4,063,064 | 12/1977 | Saunders et al. | |
| 4,088,864 | 5/1978 | Theeuwes et al. | |
| 4,324,973 | 4/1982 | Kirwan et al. | |
| 4,572,189 | 2/1986 | Smith et al. | |
| 4,580,557 | 4/1986 | Hertzmann | |
| 4,587,396 | 5/1986 | Rubin | |
| 4,604,513 | 8/1986 | Lim | |
| 4,608,480 | 8/1986 | Bizot et al. | |
| 4,618,759 | 10/1986 | Miller et al. | |
| 4,626,649 | 12/1986 | Dupeyrat et al. | |
| 4,626,999 | 12/1986 | Bannister | |
| 4,638,145 | 1/1987 | Sakuma et al. | |
| 4,707,596 | 11/1987 | Hohberg | |
| 4,710,604 | 12/1987 | Shirasu et al. | |
| 4,720,618 | 1/1988 | Stamer et al. | |
| 4,734,558 | 3/1988 | Nakano et al. | |
| 4,806,728 | 2/1989 | Salzer et al. | 219/121.63 |
| 4,820,899 | 4/1989 | Hikima et al. | 219/121.76 |
| 4,843,209 | 6/1989 | Milligan | 219/121.63 |
| 4,894,115 | 1/1990 | Eichelberger et al. | 219/121.69 |
| 4,906,813 | 3/1990 | Gajdos | 219/121.68 |
| 4,910,377 | 3/1990 | Matsutani et al. | 219/121.19 |
| 4,952,770 | 8/1990 | Hayashi | 219/121.67 |
| 5,019,397 | 5/1991 | Wong et al. | 424/473 |

(List continued on next page.)

FOREIGN PATENT DOCUMENTS

| | | | |
|---|---|---|---|
| 35 16759 A 1 | 5/1985 | Germany. | |
| 56-4391 | 1/1981 | Japan | 219/121.71 |
| 57-28693 | 2/1982 | Japan | 219/121.7 |
| 2-108484 | 4/1990 | Japan | 219/121.71 |
| WO 91/01884 | 2/1991 | WIPO. | |
| WO9401239 | 1/1994 | WIPO. | |

OTHER PUBLICATIONS

Derwent's Abstract, No. 95-288043/38, week 9538, Abstract of JP 7184981 (Kyowa Hakko Kogyo KK et al), 25 Jul. 1995 (25 Jul. 1995).

*Primary Examiner*—Teresa J. Walberg
*Assistant Examiner*—Gregory L. Mills
*Attorney, Agent, or Firm*—D. Byron Miller; Felissa H. Cagan; Steven F. Stone

[57] ABSTRACT

A method of laser drilling a delivery port (37) in a beneficial agent dispenser (30) is disclosed. A dispenser (30) has a compartment (32) formed by a wall (31) for containing a beneficial agent (33) to be delivered. A laser beam is employed for burning at least partially through the wall (31). The laser beam and the dispenser (30) are positioned relative to one another such that the laser beam is aimed at a predetermined port site (35) on the dispenser (30). The laser beam is turned off (unenergized) during the positioning period. The laser beam is then energized and moved relative to the dispenser (30) for scribing a delivery port (37) proximate the port site (35). The scribing motion moves the laser beam from the port site (35) along a course (37). Preferably the course (37) is closed. The scribing motion causes the burning of the wall (31) by the laser beam to scribe the delivery port (37). The positioning motion and the scribing motion are controlled by a scanning system (16). The laser source (13) beam is energized during the scribing motion for burning the wall (31) forming the delivery port (37) therein for subsequent delivery of the beneficial agent (33) therethrough.

18 Claims, 5 Drawing Sheets

U.S. PATENT DOCUMENTS

| | | | |
|---|---|---|---|
| 5,021,053 | 6/1991 | Barclay et al. | 604/892.1 |
| 5,049,721 | 9/1991 | Parnas et al. | 219/121.68 |
| 5,117,087 | 5/1992 | Baker et al. | 219/121.7 |
| 5,256,440 | 10/1993 | Appel. | |
| 5,279,832 | 1/1994 | Greissinger et al. | 424/467 |
| 5,294,770 | 3/1994 | Riddle et al. | 219/121.7 |
| 5,376,771 | 12/1994 | Roy | 219/121.71 |
| 5,462,741 | 10/1995 | Carr et al. | 424/473 |

FIG. 9
FIG. 10
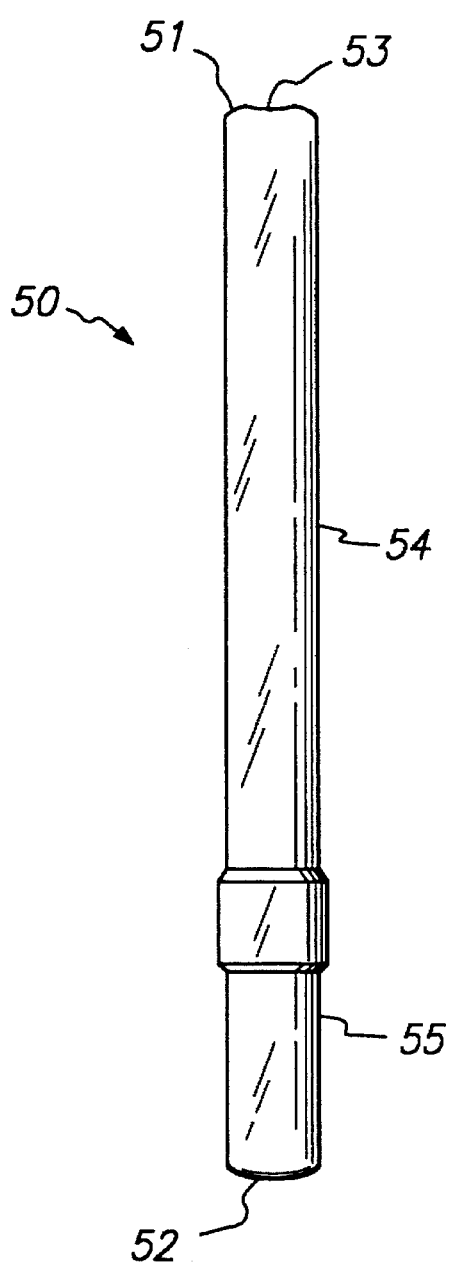
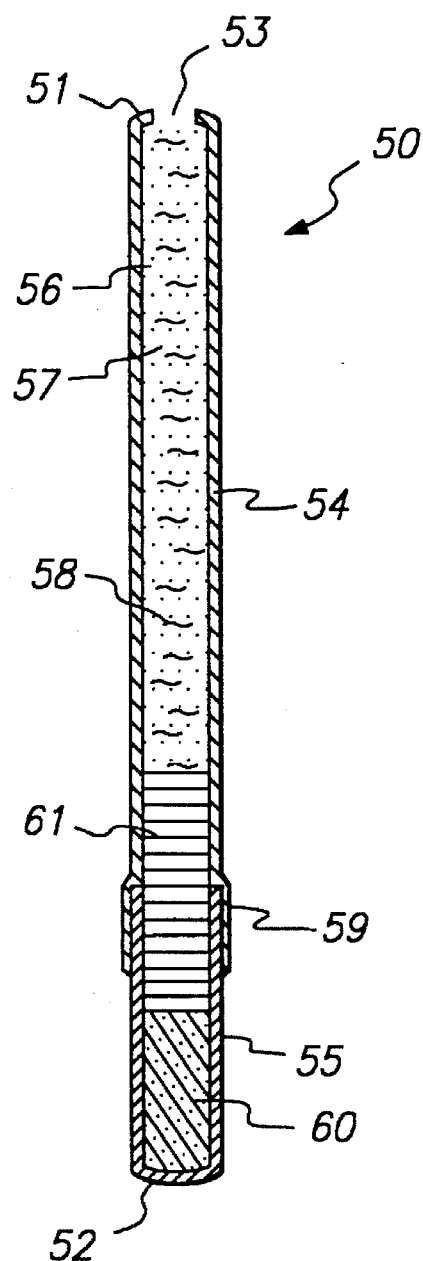

5,658,474

METHOD AND APPARATUS FOR FORMING DISPENSER DELIVERY PORTS

TECHNICAL FIELD

This invention relates to the use of a laser to form a delivery port in a beneficial agent dispenser, and more particularly to a method and apparatus for forming a delivery port having a maximal passage area while requiring minimal mass removal and minimal laser energy.

BACKGROUND ART

Saunders et al U.S. Pat. No. 4,063,064; Theeuwes et al U.S. Pat. No. 4,088,864; and Geerke et al U.S. Pat. 5,294,770 all disclose machines for transporting pharmaceutical tablets from a tablet reservoir to a laser treatment (ie, drilling) station where the tablets are treated (ie, drilled) by a laser. U.S. Pat. No. 5,294,770 additionally discloses laser drilling (ie, by burning) of multiple drug release ports in a single pharmaceutical tablet. Each delivery port is formed by a single pulse of a laser beam. Each port is formed independently of the other delivery ports on the tablet. Thus, the combined delivery port area of these multiple ports is simply the sum of the area of each of the ports. Since the area burned away by each laser pulse is dependent of the power of the laser pulse, the laser drilling of multiple ports requires proportionally more power.

In general the diameter of a laser drilled release port, such as disclosed in U.S. Pat. No. 5,019,397, is limited by the laser power available and the thickness and composition of the material being laser drilled. Osmotic drug dispensers typically have very thin (eg, less than 2 mm thickness) polymeric (eg, cellulose-based polymers) membrane walls. At present, most commercially sold lasers have a maximum power output of up to about 500 watts. Thus, a laser operating at 500 watts power output drilling through a cellulosic membrane having a thickness of only 0.1 mm can only drill an orifice having a diameter of up to about 0.7 mm. Unfortunately, dispensers are now being developed which require orifices having diameters of up to about 10 mm and even larger.

DISCLOSURE OF THE INVENTION

The present invention provides an improved method for forming delivery ports in beneficial agent dispensers using a laser.

This invention further provides such a method which forms delivery ports having maximal passage area while requiring minimal laser energy.

This invention further provides a method of laser drilling delivery ports having diameters greater than the drilling diameter of conventional drilling laser beams using conventional lasers having drilling beams of conventional power and drilling diameter.

In addition to a laser drilling method and apparatus, the present invention also provides an improved method and apparatus for marking (eg, placing an identification symbol on) a workpiece, such as a pharmaceutical tablet or a beneficial agent dispenser, using a laser.

Briefly, the present invention provides a method of forming a delivery port in a beneficial agent dispenser. The dispenser has a compartment formed by a wall and containing the beneficial agent to be delivered. A laser beam having an effective burning diameter burns at least partially through the wall. The dispenser is conveyed along a path to a point where the laser is aimed at a predetermined port site on the dispenser (ie, the laser beam path intersects the predetermined port site on the dispenser). The laser source is energized and scribing relative motion is established between the laser beam path and the dispenser for scribing a delivery port proximate the port site. The laser source emits a laser beam during at least a portion of the scribing motion to burn the dispenser wall. The laser beam may be fired continuously or in a pulsed manner during the scribing motion. If fired in a pulsing mode, preferably the pulsing of the laser and the speed of the scribing motion are selected so that a plurality of overlapping burn holes are formed through the dispenser wall. The dispenser delivery port is formed by the continuous/pulsed beam burning the scribed pattern (eg, a line, a circle, a square, etc) in the dispenser wall.

In a similar manner, the apparatus and method of the present invention may be used to scribe an identifying mark (eg, a symbol, a trademark or other identifying text) on an object such as a pharmaceutical agent dispenser by laser surface burning, as opposed to laser drilling, the mark on the object.

BRIEF DESCRIPTION OF THE DRAWINGS

Further objects and advantages of the present apparatus and method of forming a delivery port, and/or forming an identifying mark, on an agent dispenser will become apparent from the following detailed description and drawings (not drawn to scale) in which:

FIGS. 9 and 10 are side and side sectional views of an agent dispenser having a delivery port scribed and laser drilled in accordance with the present invention embodiment;

MODES FOR CARRYING OUT THE INVENTION

Figure 1:
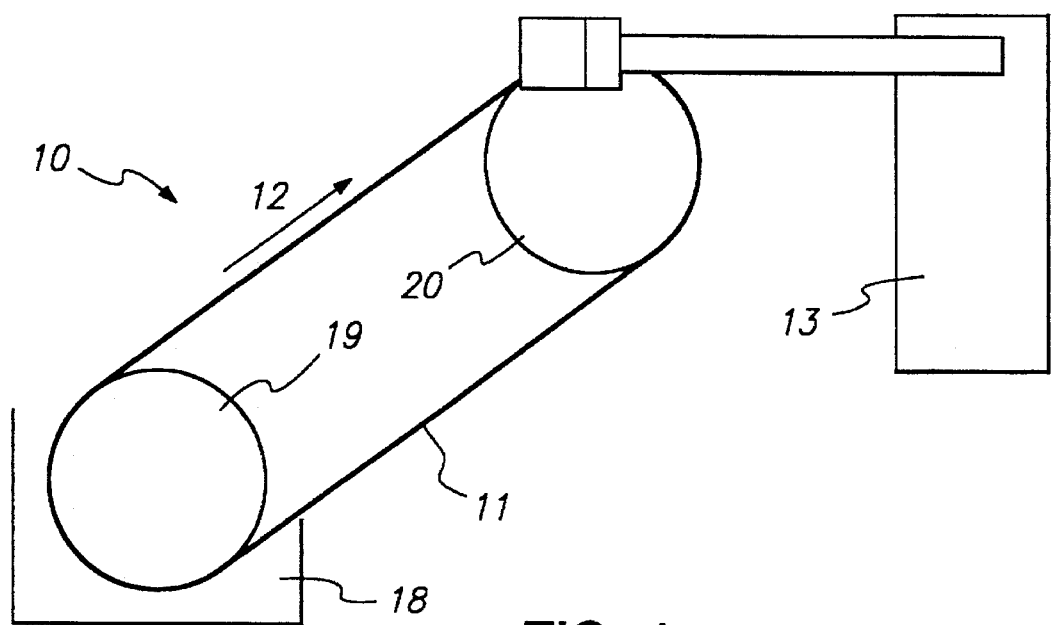
FIG. 1 is a side view of a dispenser treating apparatus showing the basic elements required to form the delivery ports.
Figure 2:
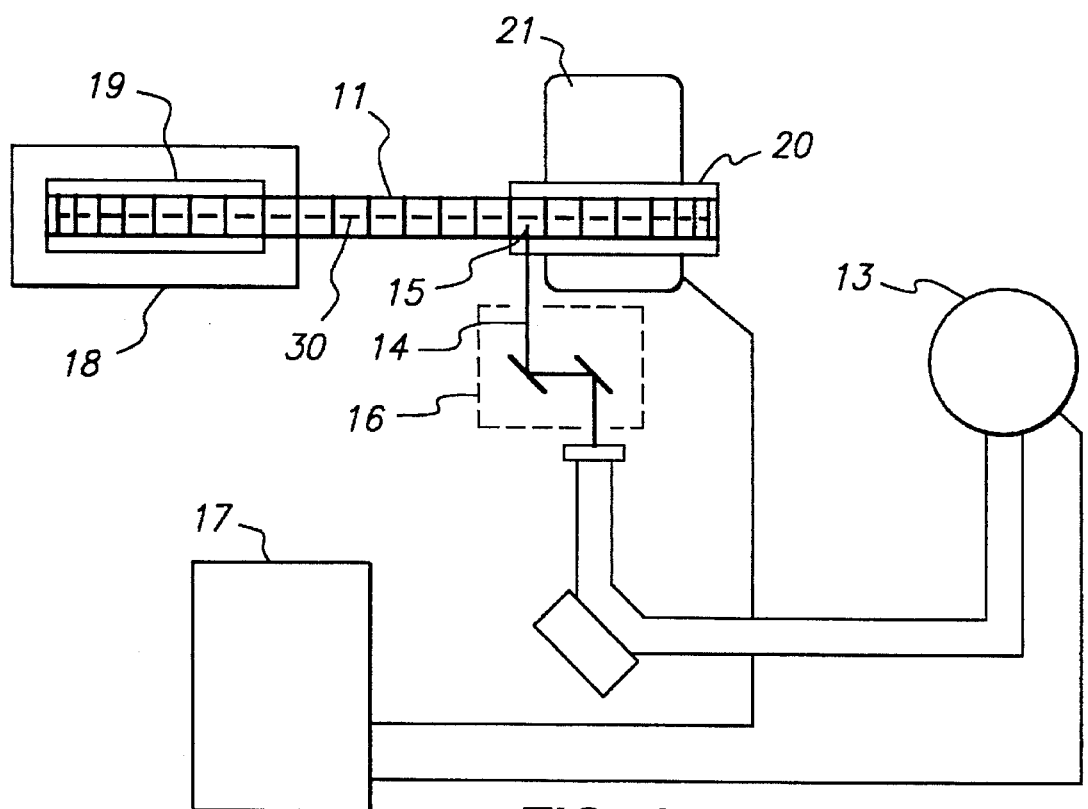
FIG. 2 is a top view of the dispenser treating apparatus of FIG. 1.
Figure 11:
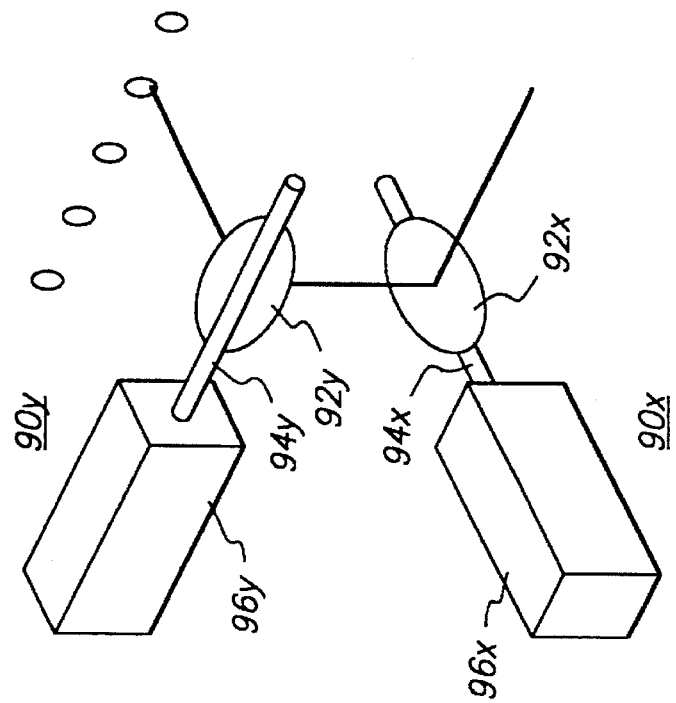
FIG. 11 is a perspective view of a laser scanning system showing a scribing control means including an X deflection mirror and a Y deflection mirror.

As shown in FIGS. 1 and 2, dispenser treatment apparatus 10 treats a series of dispensers 30 with laser energy proximate a predetermined port site on each dispenser. An endless conveyer 11 moves individual dispensers 30 along dispenser path 12 (in the direction of the arrow) from a supply end of the treatment apparatus to a collection end. Laser source 13 provides laser energy along a laser beam path 14 which crosses the dispenser path 12 defining an intersection zone 15 common to both paths 12, 14. Relative motion between each of the dispensers 30 and the laser beam is established by the motion of the endless conveyer 11 and by a suitable laser scanning system 16 disclosed in more detail hereinafter (FIG. 11).

The treatment apparatus 10 has laser ready windows during which the laser source 13 may be fired. A controller 17 is responsive to the relative motion between the dispenser 30 and the laser beam and responsive to the laser ready windows for energizing the laser beam. A suitable dispenser treatment apparatus 10 and controller 17 are disclosed in Geerke et al U.S. Pat. No. 5,294,770, the disclosures of which are incorporated herein by reference.

Supply hopper 18 is positioned proximate the supply end of the dispenser path 12 for containing a reserve of untreated dispensers 30 which are loaded onto the conveyer 11 for treatment with the laser energy. The endless conveyer 11 is preferably a carrier chain formed by carrier links extending from the supply hopper 18 through the intersection zone 15 to the collection end and back to the supply hopper 18 for moving the dispensers 30 along the dispenser path 12 and through the intersection zone 15 for treatment. A supply wheel 19 mounted within the supply hopper 18 engages the supply end of the conveyer 11, permitting the dispensers 30 to load onto the carrier chain. A collection wheel 20 mounted proximate the collection end of the dispenser path 12 engages the collection end of the conveyer 11. The collection wheel 20 is positioned higher than the supply wheel 19 to create a positive slope along the dispenser path 12 which raises the dispensers 30 out of the dispenser supply hopper 18 up to the intersection zone 15.

A suitable drive device such as motor 21 moves the endless carrier chain around the wheels 19 and 20, and conveys the dispensers 30 along the dispenser path 12. In the embodiment of FIG. 1, collection wheel 20 is a drive wheel connected to the drive motor 21 and lower wheel 19 is a free turning idler wheel. The upper drive wheel 20 pulls against the drag of the chain links and the idler wheel 19 to hold the carrier chain taut along the inclined dispenser path 12.

The basic steps of laser scribing a delivery port in a beneficial agent dispenser is described below.

The apparatus and method of the present invention can be used to form delivery ports in pharmaceutical agent dispensers, eg, dispensers which are adapted to be implanted in, or swallowed by, a patient and thereafter deliver a pharmaceutical agent (eg, a drug) to the patient. Two particularly useful dispensers which can be used with the present invention are osmotically driven and are designated by the reference numerals 30a and 30b in FIG. 3. Dispenser 30a is an elementary osmotic pump dispenser while dispenser 30b is a push-pull type osmotic dispenser. Dispenser 30a has a semipermeable membrane wall 31. Wall 31 surrounds and forms an internal compartment 32. Internal compartment 32 comprises a dispensable drug 33, identified by dots, and an optional osmagent 34 represented by dashes. Wall 31 is semipermeable, ie, it is permeable to the passage of an exterior fluid (eg, water) present in the biological environment of use (eg, the gastro-intestinal (GI) tract of an animal body), and is substantially impermeable to the passage of drug 33 and optional osmagent 34. Wall 31 preferably comprises a thin cellulosic membrane. Because wall 31 is substantially impermeable to drug 33, dispenser 30a must have at least one delivery port provided through wall 31 at port site 35a in order to deliver drug 33 to the biological environment of use. When dispenser 30a is placed in an aqueous environment (eg, when dispenser 30a is swallowed by a patient), water from the patient's GI tract permeates through wall 31 and forms an aqueous solution or suspension of drug 33. As more water permeates through wall 31, the aqueous drug solution or suspension is pumped out of the delivery port 38a, which port is defined by the laser scribed channel 37a, and into the patient's GI tract.

Like dispenser 30a, dispenser 30b also has a wall 31 which surrounds and forms an internal compartment 32 containing a drug and an optional osmagent or osmopolymer 34. However, compartment 32 of dispenser 30b also comprises an expandable hydrogel 36 identified by vertical lines. The drug-containing composition 33, 34 and the expandable hydrogel 36 are in laminar arrangement, and they cooperate with wall 31 for the effective delivery of drug 33 through the delivery port formed at port site 35b. Like the wall 31 of dispenser 30a, the wall 31 of dispenser 30b is semipermeable, ie, it is permeable to a liquid solvent (ie, water) present in the environment of use but impermeable to the beneficial agent 33 and is preferably a thin cellulosic membrane. When dispenser 30b is placed in an aqueous environment (eg, when dispenser 30b is swallowed) water from the environment permeates through wall 31 and is absorbed by the expandable hydrogel 36, causing it to swell. As hydrogel 36 swells, it pushes against the beneficial agent 33 which is thereby forced out of the dispenser 30b through the delivery port 38b defined by the laser scribed channel 37b and into the environment of use. In both dispensers 30a and 30b, the outward movement of the liquid solution or suspension of beneficial agent 33 pushes central plugs 39a and 39b (positioned within the laser scribed channels 37a and 37b, respectively) away from the delivery ports 38a and 38b, respectively. In the push-pull type dispenser 30b, it is important to scribe the delivery port 38b adjacent to the beneficial agent composition 33, 34 and to position the expandable hydrogel 36 at the "closed" end of the dispenser 30b.

The beneficial agent or drug 33 may be a pharmaceutical substance (eg, a drug) which is placed in the dispensers 30a and/or 30b for metered release in vivo over time. Other potential applications of the dispensers 30a and/or 30b include the release of a catalyst for a chemical process, the release of nutrients for aquatic feeding, and the release of fertilizer for agricultural growth.

The next step in the method of the present invention is to provide a laser source which produces laser energy eg, in the form of a beam along a laser energy/beam path. The laser beam has sufficient power to be capable of burning an effective burning bore at least partially through the wall 31. The energy of the laser beam is absorbed by the wall 31 at the intersection zone 15 creating sufficient heat to vaporize the wall material. Laser beams typically have a circular cross-section with most of the energy being concentrated in the center of the beam. The effective burning bore of the laser beam is the diameter of the hole formed in wall 31 when there is no relative motion between the dispenser and the beam. The effective burning bore depends on the cross-sectional area of the laser beam at the intersection zone 15, the power of the laser and the thickness and composition of the wall material being laser drilled.

The next step in the method of the present invention is to position dispenser 30a and/or the laser beam such that the laser beam path intersects dispenser 30a at a predetermined port site 35a on the dispenser. The laser source is usually turned off (un-energized) during the positioning step. The positioning of the laser beam is controlled by laser scanning system 16, while the positioning of the dispenser 30a is controlled by the movement of conveyor 11 (conveyor 11 is not shown in FIG. 3 for ease of illustration) which conveys the dispensers 30a and 30b along the X axis in the direction of the arrow in FIG. 3. The positioning of the laser beam path 14 and the positioning of the dispensers 30a and 30b determines the position of the delivery ports 38a and 38b, respectively, on the dispensers 30a and 30b, respectively. The positioning motion also moves the dispensers 30a and 30b relative to the laser beam path 14 such that the beam is aimed initially at dispenser 30a and subsequently at dispenser 30b, ie, the laser beam path 14 is initially aimed at port site 35a on dispenser 30a, and following the scribing of channel 37a, the laser beam path is aimed at port site 35b on dispenser 30b which is the next dispenser in line on conveyer 11. Alternatively, the positioning motion may move the laser path 14 and/or the dispensers such that the laser beam path 14 is subsequently aimed at a second or third site on the same dispenser to produce a multi-port dispenser.

The next step in the method of the present invention is to establish scribing relative motion between the laser beam path 14 and the dispenser 30a for scribing a channel 37a proximate the port site 35a. During the scribing motion, the laser source 13 is turned on (energized) producing a laser beam which causes burn removal of the wall material proximate the port site 35a. The scribing motion is controlled by (i) the movement of the dispenser 30a in the X direction, which movement is controlled by the movement of conveyor 11, (ii) the movement of the laser beam path, which movement is controlled by the scanning system 16, or a combination thereof. The scribing motion determines the size and shape of the delivery port. The scribing motion causes the laser beam to move relative to dispenser 30a, from the port site 35a along a generally circular course 37a and back to the port site 35a. The scribing motion causes the laser beam to burn the wall 31 along channel 37a which defines delivery port 38a. The thus formed delivery port 38a allows subsequent delivery of the beneficial agent or drug 33 therethrough.

Figure 3:
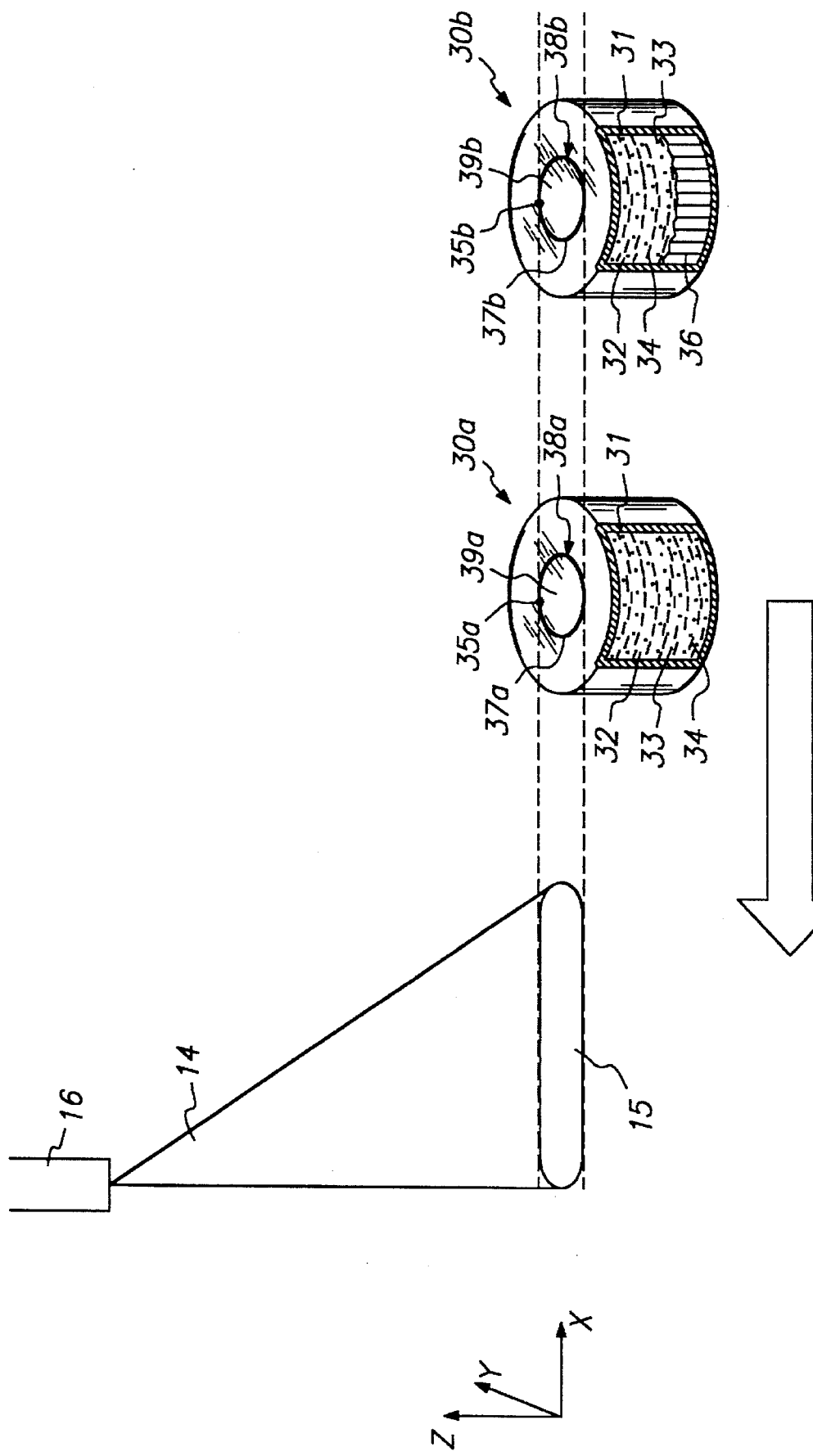
FIG. 3 is a perspective view of two adjacent dispensers, with parts thereof shown in section, showing (i) the conveyor motion for positioning the dispensers in the intersection zone with the laser beam path and (ii) the scribing relative motion for scribing the delivery ports.

As shown in FIG. 3, the port site 35a is the starting point of the circular course 37a and preferably is also the terminal point. As such, the channel 37a forms a closed course which completely surrounds round central plug 39 of wall material. The term "closed" in connection with a laser scribed channel refers to a scribed channel of any shape which starts at a starting point and returns the laser beam to substantially the same starting point. Plug 39a is adapted to be removed to allow drug 33 to be dispensed through port 38a. Plugs 39a and 39b on osmotic dispensers 30a and 30b are pushed away from ports 38a and 38b, respectively, by the osmotic pumping of drug solution or suspension out of dispenser 30a. In nonosmotic dispensers it may be necessary to remove the central plug 39 before the dispenser can become fully operative.

In FIG. 3, the scribing motion causes the burning of the wall 31 by the laser beam, forming a circular channel 37a surrounding a central plug 39a of wall material. The passage area of the large delivery port 38a is equal to the area of central plug 39a plus the area of burned channel 37a. The central plug 39a is pushed out of the delivery port 38a by osmotic pressure and represents delivery port area that does not require burning by the laser. That is, most of the passage area of the delivery port 38a is formed by the central plug 39a, rather than the area of the burned channel 37a, and hence most of the area of the delivery port 38a is created without burning of wall 31 by the laser, and without generating burned debris or requiring laser energy. The larger passage area permits delivery of larger quantities of the beneficial agent per unit of time into the environment of use.

In the embodiment shown in FIG. 3, the scribing motion moves the laser beam along generally circular channels 37a and 37b to scribe generally round delivery ports 38a and 38b. The channel 37 may be non-circular as shown in FIGS. 4A through 4D. A round delivery port has the maximum passage area for the amount of laser drilling (burn removal mass) and is the preferred shape. That is, a circular channel 37 produces a round delivery port 38 with the least debris per square unit of port area. The scribed channel may be slightly out-of-round due to manufacturing tolerances. The endless conveyor 11 may vary in speed during manufacture, or generally slow down with age. The laser scanning system 16 may be imperfect, or vibrate during operation, or drift out of calibration. In practice, a circular channel 37 resulting in a round delivery port 38 may be merely a desirable goal which is theoretically possible.

Figure 4C:
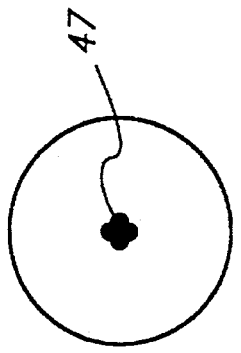
FIGS. 4A through 4D are perspective views of agent dispensers having an oval shaped delivery port, a slot shaped delivery port, a bore cluster delivery port, and a polygon shaped delivery port, respectively, all scribed in accordance with the present invention.
Figure 4E:
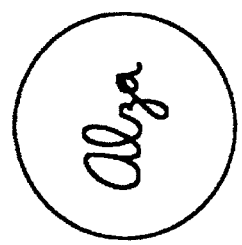
FIG. 4E is a perspective view of an agent dispenser having an identifying marking scribed in accordance with the present invention.
Figure 4B:
Figure 4D:
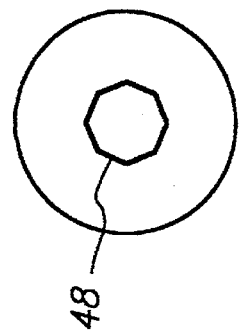
Figure 4A:
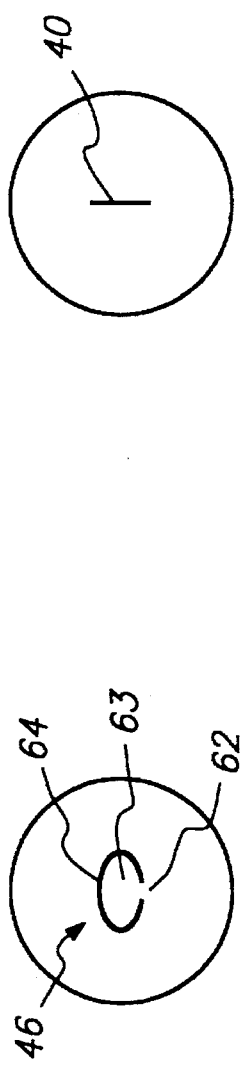

Alternatively, the delivery port may be non-circular, such as the polygon shaped port 48 shown in FIG. 4D, or the channel defining the delivery port may be non-closed such as the C-shaped channel 64 shown in FIG. 4A or the slot shaped delivery port 40 shown in FIG. 4B. The C-shaped channel 64 forms a delivery port 46 having a generally oval shape with a major port dimension and a minor port dimension. The unburned wall portion 62 functions as a hinge permitting the central plug 63 to fold away to the hinged side like a flap under the force of the internal osmotic pressure. Unlike plugs 39a and 39b, which are shed when osmotic dispensers 30a and 30b begin pumping the liquid solution or suspension of drug 33, the hinged central plug 63 remains attached to the dispenser and is not shed into the environment of use.

The minimum minor port dimension of a delivery port formed according to the present invention may be only one burning bore diameter while the minimum major port dimension of the delivery port is at least about twice the burning bore diameter and preferably at least about 5 times the burning bore diameter. An example of a delivery port 40 having a minor port dimension of only one burning bore diameter and a major port dimension comprising a plurality of burning bore diameters is shown in FIG. 4B. Since the minor port dimension (ie, the width) of delivery port 40 is limited to the diameter of the burn bore, the area of port 40 is limited. Thus, elongated slot shaped delivery port 40 is typically used only when small area ports are needed or when drilling a flexible wall material which allows the slot shaped port 40 to bulge open during the dispensing of the beneficial agent or drug 33.

FIG. 4C shows a delivery port 47 having a major port dimension of about 2 burning bore diameters and a minor port dimension of about 2 burning bore diameters. Port 47 is formed by a pulsed laser beam which produces a cluster of four adjacent laser burned bores. The minimum number of adjacent or clustered burn bores forming a delivery port according to the present invention may be as few as two to four (see for example delivery port 47 in FIG. 4C) or as many as several hundred or even several thousand when forming large polygon shaped ports (such as port 48 in FIG. 4D) using a pulsed firing laser. The minimum dimension of the delivery port may be much greater than the effective burning bore of the laser beam, resulting in a large oval shaped delivery port 46 as shown in FIG. 4A or a large polygon shaped delivery port 48 shown in FIG. 4D. Port 48 is formed by scribing a series of straight lines with the laser. The polygon-shaped port 48 may alternatively have another geometric shape such as a triangle, square, pentagon, etc.

The laser source energization may be continuous during the scribing motion to continuously burn the wall creating a continuous scribed channel. The preferred speed of the scribing motion for a continuously energized laser beam is a function of burn removal factors such as the power of the laser, the effective burning bore, the thickness and composition of the wall, and the desired depth of the channel. If the scribing motion is too fast, the laser beam will remove too little wall material and the channel will be too shallow. If the scribing motion is too slow, the laser beam will remove all of the wall and burn into the beneficial agent formulation, ie, the channel will be too deep. Overly deep channels generate unnecessary debris, utilize unnecessary laser power, and/or unnecessarily slow down the speed of conveyor 11 and hence the manufacturing line. The following is illustrative of a typical scribing motion speed: using a laser having a power output of 25 watts and a burning bore diameter of 0.15 mm, for drilling a semipermeable cellulosic membrane having a thickness of about 0.1 mm, the scribing motion speed is about 1 m/sec.

Figure 6:
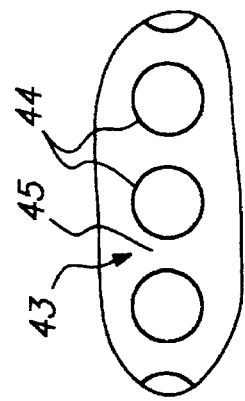
FIG. 6 is a top view of a scribed channel formed by spaced burn bores.
Figure 5:
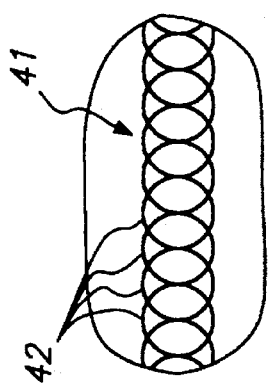
FIG. 5 is a top view of a scribed channel formed by overlapping burn bores.

The laser source energization may also be pulsed during the scribing motion to create the channel. The channel may be a continuous channel 41 formed by a series of overlapping (or tangent) burn bores 42 as shown in FIG. 5. Channel 41 is shown as a straight channel suitable for forming a linear (ie, slot shaped) port or one side of a polygon shaped port. Channel 41 could also be formed as a curved channel suitable for defining a round or oval delivery port. Alternatively an intermittent channel 43 formed by a series of closely spaced burn bores 44 can be scribed as shown in FIG. 6. The scribing motion between pulses of the laser leaves narrow connecting bridges 45 of wall material between adjacent burn bores 44. The connecting bridges 45 are sufficiently narrow that they break open between adjacent burn bores 44 when the dispenser begins dispensing the beneficial agent. Channel 43 is shown as a straight channel but could also be formed as a curved channel suitable for forming a segment of a round or oval shaped port.

Figure 8:
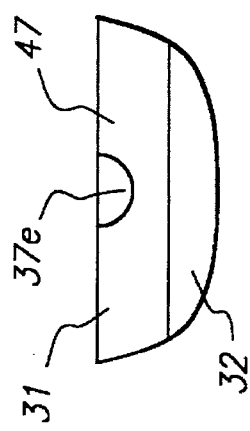
FIG. 8 is a partial sectional view of a scribed partial depth channel which is laser drilled in accordance with the present invention.
Figure 7:
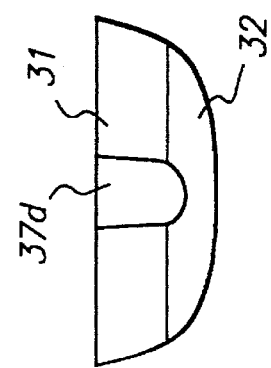
FIG. 7 is a partial sectional view of a scribed full depth channel which is laser drilled in accordance with the present invention.

FIGS. 7 and 8 are cross sectional views of portions of wall 31 and compartment 32 of dispenser 30 and illustrate variations in the depth of laser drilling which may be used in the method of the present invention. The laser source 13 may be of sufficient power or have a sufficient on-time to produce a laser beam which burns completely through the wall 31 as shown in FIG. 7 creating a deeply burned channel 37d. Deep channel 37d extends completely through the wall 31 from the outer surface down to the beneficial agent within the compartment 32. When forming a deep channel having a closed shape (eg, a deep channel having a circular shape similar to channel 37a in FIG. 3), the central plug 39a may flake off prior to use, particularly if the adhesion of wall 31 to the beneficial agent formulation is weak.

Alternatively, the laser source 13 may be of lower power or have a shorter on-time and burn only partially through the wall 31, as shown in FIG. 8, creating a shallow burned channel 37e. Shallow channel 37e extends only partially through the wall 31 leaving floor 47 along the bottom of the channel 37e. The beneficial agent in compartment 32 is not exposed to the laser due to the cover provided by the floor 47.

Unlike the deep channel embodiment (FIG. 7), the shallow channel and intermittent channel embodiments (FIGS. 8 and 6), when formed in a closed (eg, circular) shape, retain the central plug of wall material in place in the delivery port opening until the time of use. Thus, the channel floor 47 of the shallow channel 37e and the connecting bridges 45 of the intermittent channel 43 retain the central plug 39a of wall material (see FIG. 3) in position in the delivery port 38a during manufacture and storage of the dispenser 30a, thereby affording greater protection (eg, against light or UV degradation) to the beneficial agent in compartment 32. The floor 47 of the partial channel is sufficiently thin to permit the osmotic pressure that develops within the compartment 32 when the dispenser is placed in an aqueous environment to break the wall material forming the floor 47. Likewise the connecting bridges 45 between the spaced burn bores 44 of the intermittent channel 43 are spaced sufficiently close to permit the osmotic pressure that develops within the compartment 32 when the dispenser is placed in an aqueous environment to break the wall material forming the bridges 45. The pumping of the beneficial agent solution or suspension then pushes the central plug 39 away from the delivery port 38. The optimum floor 47 thickness and bridge 45 length for this "break-away" mode depends on the strength and thickness of the wall material and on the internal pressure generated within the compartment.

A channel floor and connecting bridges may be employed on the same break-away central plug. That is, the connecting bridge may be partially burned away forming a partial channel between the spaced burn bores. The floor, bridge and hinged flap embodiments generate less burn removal per square unit of passage area, and therefore require less laser energy for the same size delivery port.

Another example of an implantable osmotically driven delivery system is shown in FIGS. 9 and 10 and is identified by the number 50. FIG. 9 is a side view of system 50 while FIG. 10 is a side sectional view of system 50. Delivery system 50 comprises a delivery end 51, a trailing end 52 and a passageway 53 provided at end 51 that connects the exterior environment with the interior of delivery system 50. Passageway 53 is laser scribed through the wall of housing section 54 in accordance with the present invention. Delivery system 50 has an outer housing comprised of a first housing section 54 and a second housing section 55. The two housing sections 54, 55 have diameters which are close in size and they form a tight friction fit therebetween. There is clearance or tolerance in size to allow section 55 a sliding movement into the receiving means 59 of section 54. Sections 54 and 55 can be telescoped completely into a closed and continuous walled position. Optionally, they can be held together by heat fusion, by adhesive, or the like. Housing sections 54, 55 surround and define an internal compartment 56. Housing section 54 surrounds a beneficial agent formulation which comprises a pharmaceutical agent (eg, a drug) identified by dots 57, and a pharmaceutically acceptable carrier identified by wavy lines 58. The pharmaceutically acceptable carrier 58 may comprises more than one ingredient, such as a buffer, a surfactant or other formulation ingredients. Housing section 54 at its end distant from lead end 51 defines and forms receiving means 59. Receiving means 59 is enlarged slightly for receiving housing section 55. The wall of housing section 54 comprises a composition that is substantially impermeable to the beneficial agent formulation 57, 58 and other ingredients contained in delivery system 50. Housing section 54 is preferably substantially impermeable to the ingress of any liquids (eg, water) present in the exterior environment and serves as a means for substantially protecting a beneficial agent 57 (eg, a protein) that is unstable when exposed to the liquid. Thus, unlike wall 31 in dispensers 30a and 30b, the wall of housing section 54 is not a semipermeable membrane and may be formed of nonpermeable materials such as polymers, plastics, elastomers, etc, which can be burned by a laser. Housing section 54 substantially restricts and prevents fluid from passing therethrough and entering into compartment 56 in the region containing the beneficial agent formulation 57, 58. Housing section 55 surrounds an expandable driving member 60 (eg, an expandable hydrogel) identified by slanted lines. Expandable driving member 60 optionally comprises an osmagent, homogeneously or heterogeneously blended within the expandable driving member 60. Compartment 56 optionally comprises a layer 61, represented by horizontal lines, positioned between the beneficial agent formulation 57, 58 and the expandable driving member 60. Layer 61 preferably comprises a composition that is substantially impermeable to the passage of liquid imbibed into driving member 60 and it serves to restrict the passage of liquid present in the expandable driving member 60 into the beneficial agent formulation 57, 58; and it operates to essentially maintain the integrity of the beneficial agent layer and the driving layer. Layer 61 acts also to insure that the expanding driving force generated by the expandable driving member 60 is applied evenly and directly against the beneficial agent formulation 57, 58. The wall of housing section 55 comprises, at least in part, a semipermeable wall composition that is permeable to the passage of the liquid (eg, water) present in the exterior environment and for making available fluid to the expandable driving member 60. The wall of housing section 55 is permeable to the passage of the liquid (eg, water) present in the exterior environment and it is substantially impermeable to the passage of other ingredients contained in driving member 60. Housing 54, 55 may optionally comprise a plasticizer that imparts flexibility and workability to the wall. Housing 54, 55 is non-toxic and in a preferred embodiment, it maintains its physical and chemical integrity, that is, housing 54, 55 does not erode during the dispensing period.

In operation, delivery system 50 is placed in a biological environment of use (eg, system 50 is implanted in the body of a mammal, eg, humans or livestock) and exposed to an aqueous liquid. The aqueous liquid permeates through the semipermeable wall of housing section 55 and is absorbed by driving member 60, as the expandable driving member 60 absorbs and imbibes fluid, it expands and pushes against layer 61 causing it to slide within compartment 56 toward passageway 53. Layer 61 moves towards passageway 53, pushing the beneficial agent formulation 57, 58 through passageway 53 for delivery of the beneficial agent 57 into the biological environment of use.

FIG. 11 shows a schematic illustration of a scanning system for controlling the scribing motion of a continuously or intermittently fired laser. Laser scanning system 16 may be any suitable mechanism for systematically deflecting the laser beam such as an X-Y scanning device. The positioning of the dispenser with respect to the laser beam and the scribing relative motion are established along a first axis by a first scanning mirror and along a second axis by a second scanning mirror. The first axis may be along the direction of motion of endless conveyer 11 (see X axis—FIG. 3), and the second axis may be traverse to the direction (see Y axis—FIG. 3). Alternatively a three dimensional (see Z axis—FIG. 3) laser scanning system may optionally be used. The focal point of the laser beam can be moved along the Z axis by appropriately moving a beam focusing lens in the Z direction.

X axis scanner 90X includes X deflection mirror 92X mounted on pivoting shaft 94X (extending in the Y direction) which is displaced by X galvanometer 96X. Y axis scanner 90Y includes Y deflection mirror 92Y mounted on pivoting shaft 94Y (extending in the X direction) which is displaced by Y galvanometer 96Y. The galvanometers are servo-like rotary drives having low mass with minimal inertia, which are responsive to X-Y control voltages from controller 17. The displacement of the mirrors may be smooth in response to a smoothly changing control voltage, to provide a uniform rate of deflection of the laser beam. Alternatively, the displacement may be incremental in response to a step change in control voltage, for deflecting the laser beam by increments.

In a pulsed laser beam embodiment such as FIGS. 5 and 6, each rotational step of the mirrors may coincide with a pulse of laser energy. This one pulse for one step arrangement provides a progressively spaced but unique XY location for each laser pulse. Polygon shaped delivery ports (see FIG. 4D) may be easily formed by rotationally stepped mirrors. The straight line between each pair of successive vertices is created by a series of uniform X and Y steps. At each vertice, the values of the X and Y steps change to create the next straight line forming the polygon. The motion of the endless conveyer 11 may be constant to provide a constant movement of the dispensers 30 along the X axis. Alternatively, the conveyer 11 may be step advanced by a stepping motor.

In the embodiment of FIG. 3, the relative motion along the X axis is the sum of the motion of the endless conveyer 11 plus the motion due to the X deflection mirror; while the relative motion along the Y axis is due only to the Y deflection mirror.

The method of forming a delivery port in an agent dispenser disclosed herein may also be employed to mark an identification symbol on the surface of a plurality of workpieces such as dispensers 30 presented in a series. One difference between forming a delivery port and marking an identification symbol is simply the relative power of the laser which is required. With delivery port formation, the laser must have sufficient power to burn substantially through the wall 31. On the other hand, the marking is formed by burning due to the heat of the laser energy, and may be accomplished by disturbing, discoloring or carbonizing the surface material. Alternatively, the identification symbol maybe formed by burning the interior material as well as the surface material thereover. Such deep burning may form a delivery port which also functions as an identification marking.

The sequence of steps for laser marking an identification symbol are as follows. First, laser source 13 produces laser energy along a laser beam path for marking the surface of each workpiece. Relative positioning between the laser beam path and the presented workpiece 30 is established for positioning the laser energy at a predetermined marking site on the presented workpiece. Scribing relative motion is established between the laser beam and the workpiece for defining the identification symbol proximate the marking site. The laser source is energized during the scribing motion to produce the laser energy for marking the surface forming the identification symbol thereon for subsequent identification of the workpiece.

The identification symbol may be a stroke based symbol such as an alpha-numeric formed by at least one stroke. The simple single stroke numeral "1" may be formed in substantially the same manner as laser drilled slot shaped delivery port 40 shown in FIG. 4B. The defining relative motion defines the stroke (or strokes) for marking the workpiece. The identification symbol may be at least one solid area formed by a plurality of adjacent strokes defined by the relative motion. Alternatively, the scribing motion can define printed text and/or a trademark as shown in FIG. 4E. In the surface marking embodiments, only the surface of the workpiece is affected by the laser energy. Therefore the laser beam may have a larger diameter beam for forming a wider more visible stroke than in the delivery port drilling embodiments. This shallow marker burning generates less debris and can be accomplished by a faster scribed beam with lower energy than the beam needed to form delivery ports.

It will be apparent to those skilled in the art that the objects of this invention have been achieved by providing an improved method for forming delivery ports in beneficial agent dispensers. Clearly various changes may be made in the structure and embodiments shown herein without departing from the concept of the invention. Further, features of the embodiments shown in the various figures may be employed with the embodiments of the other figures. Therefore, the scope of the invention is to be determined by the terminology of the following claims and the legal equivalents thereof.

I claim:

1. A method of forming a delivery port in a beneficial agent dispenser, comprising:

providing a dispenser having a compartment formed by a wall, and containing a beneficial agent to be delivered;

providing a laser source which produces laser energy along a laser energy path, the laser energy being capable of burning a bore of predetermined dimension at least partially through the wall of the dispenser;

positioning the dispenser relative to the laser energy path such that the laser energy path intersects the dispenser at a predetermined port site on the dispenser;

establishing scribing relative motion between the laser energy path and the dispenser for scribing a channel at least partially surrounding a removable central plug, the channel and the removable plug defining a delivery port proximate the port site; and energizing the laser source during the scribing motion to produce laser energy which forms the delivery port in the wall, the delivery port having at least one dimension which is greater than the bore dimension.

2. The method of claim 1, wherein the laser source is continuously energized during the scribing motion to form a continuous channel in the wall.

3. The method of claim 1, wherein the laser source is pulsed energized during the scribing motion.

4. The method of claim 3, wherein the pulsed laser energy forms a series of overlapping burn bores.

5. The method of claim 3, wherein the pulsed laser energy creates a series of spaced burn bores, the spacing between adjacent burn bores being sufficiently close to permit the wall material to break between adjacent burn bores when the beneficial agent is dispensed through the delivery port.

6. The method of claim 1, wherein the laser energy scribes a delivery port having a predetermined shape.

7. The method of claim 6, wherein the delivery port shape is closed.

8. The method of claim 6, wherein the delivery port is generally round.

9. The method of claim 6, wherein the delivery port is slot-shaped.

10. The method of claim 6, wherein the delivery port is polygon shaped.

11. The method of claim 1, wherein the delivery port has a major port dimension and a minor port dimension, the minor port dimension being at least the dimension of the bore, the major port dimension being at least about 2 times the dimension of the bore.

12. The method of claim 1, wherein the wall comprises a semipermeable membrane and the compartment contains an osmotically active agent, whereby the beneficial agent is pumped through the delivery port by osmotic pressure.

13. The method of claim 1, wherein the laser energy burns completely through the wall.

14. The method of claim 1, wherein the laser energy burns partially through the wall, the portion of the wall remaining unburned being sufficiently thin to permit the wall material to break when the beneficial agent is delivered out of the dispenser through the delivery port.

15. The method of claim 1, wherein the positioning and the scribing between the laser beam path and the dispenser define a plurality of delivery ports in the dispenser.

16. The method of claim 1, wherein the scribing relative motion is established by displacing a scanning mirror which causes the laser beam path to move relative to the dispenser.

17. The method of claim 16, wherein the scribing relative motion is established along a first axis by displacement of a first scanning mirror and established along a second axis by displacement of a second scanning mirror.

18. The method of claim 16, wherein the scribing relative motion is established by displacement of the scanning mirror plus movement of the dispenser.

* * * * *